(12) United States Patent
LoRusso

(10) Patent No.: US 7,842,057 B2
(45) Date of Patent: *Nov. 30, 2010

(54) APPARATUSES AND METHODS FOR TRANSCLERAL CAUTERY AND SUBRETINAL DRAINAGE

(76) Inventor: Frank J. LoRusso, 8515 Hetton Heights, San Antonio, TX (US) 78250

( * ) Notice: Subject to any disclaimer, the term of this patent is extended or adjusted under 35 U.S.C. 154(b) by 1076 days.

This patent is subject to a terminal disclaimer.

(21) Appl. No.: 11/522,876

(22) Filed: Sep. 18, 2006

(65) Prior Publication Data

US 2007/0016186 A1   Jan. 18, 2007

Related U.S. Application Data

(63) Continuation of application No. 10/099,039, filed on Mar. 15, 2002, now Pat. No. 7,122,042.

(60) Provisional application No. 60/276,068, filed on Mar. 15, 2001.

(51) Int. Cl.
*A61B 17/32* (2006.01)

(52) U.S. Cl. ...................................... 606/167; 604/117

(58) Field of Classification Search ............... 606/41, 606/166, 167, 170, 172, 174; 604/51, 117, 604/187, 290
See application file for complete search history.

(56) References Cited

U.S. PATENT DOCUMENTS

| | | | | |
|---|---|---|---|---|
| 4,940,468 A | * | 7/1990 | Petillo | 606/170 |
| 5,320,608 A | * | 6/1994 | Gerrone | 604/117 |
| 5,409,457 A | * | 4/1995 | del Cerro et al. | 604/521 |
| 5,971,953 A | * | 10/1999 | Bachynsky | 604/90 |
| 7,122,042 B2 | * | 10/2006 | LoRusso | 606/167 |

\* cited by examiner

*Primary Examiner*—Anhtuan T. Nguyen
*Assistant Examiner*—Victor X Nguyen
(74) *Attorney, Agent, or Firm*—Thomas, Kayden, Horstemeyer & Risley, LLP.

(57) ABSTRACT

Apparatuses for transcleral cautery and subretinal drainage are provided. One such embodiment includes a barrel section, a needle section extending from the barrel section, and a scleral depressor section at least partially surrounding an intermediate portion of the needle section. A cautery section may also be defined between the scleral depressor section and the distal end of the needle section. Methods are also provided.

10 Claims, 4 Drawing Sheets

APPARATUSES AND METHODS FOR TRANSCLERAL CAUTERY AND SUBRETINAL DRAINAGE

CROSS-REFERENCE TO RELATED APPLICATION

This application is a continuation application that claims the benefit of and priority to U.S. application Ser. No. 10/099,039, filed on Mar. 15, 2002 now U.S. Pat. No. 7,122,042, which claims the benefit of and priority to U.S. provisional application, entitled "Retinal Inserted Drainage/Cautery Apparatus," having Ser. No. 60/276,068, filed Mar. 15, 2001, both of which are entirely incorporated herein by reference.

TECHNICAL FIELD

The present invention is generally related to retinal surgery and, more particularly, is related to apparatuses and methods for transcleral cautery and subretinal drainage.

DESCRIPTION OF THE RELATED ART

In retinal surgery, for example to treat a retinal detachment condition, the time-honored approach to subretinal fluid drainage is a scleral cut-down from outside the eye ("ab externo") making an opening large enough to visualize and cauterize the choroid. The scleral cut-down and the resulting large opening in the sclera are known as a sclerotomy. In this procedure, choroidal cautery (i.e., burning or searing of a penetrated portion of the choroid) is performed to minimize hemorrhage from the choroid. Typically, a small needle attached to a tuberculin syringe with the plunger removed is then inserted through the sclerotomy, through the cauterized choroid, through the retinal pigment epithelium ("RPE"), and into the subretinal space containing the subretinal fluid ("SRF"). The positive pressure of the eye and capillary action results in the SRF passing from the subretinal space through the needle into the tuberculin syringe and, therefore, out of the eye.

To save time associated with the foregoing procedure, many surgeons began performing a different procedure. In particular, a small needle attached to a tuberculin syringe with the plunger removed is inserted ab externo directly through the sclera, i.e., without first making a sclerotomy. The needle then is passed through the choroid, without first cauterizing it, through the RPE, and then into the subretinal space containing the SRF. This procedure typically is performed under direct visualization while using a binocular indirect ophthalmoscope (or BIO) to look directly into the eye. One disadvantage of this more recently adopted procedure is that hemorrhage from the choroid occurs because, unlike in the older procedure, the choroid is not cauterized. In an attempt to prevent this complication, some surgeons elevate the intraocular pressure by tightening a scleral buckle (i.e., a belt-like or tourniquet-like device) encircled around the eye or a portion of the eye to tamponade the choroid (i.e., increase the pressure on the choroid). Although this modification may decrease the occurrence of hemorrhage from the choroid, it does not significantly minimize or eliminate it. Thus, even when using the foregoing modified procedure, hemorrhage typically still occurs, and sometimes is severe. Since subretinal blood can be very toxic to the retina, hemorrhage may result in markedly decreased vision, thus, limiting or defeating the effects of the retinal surgery.

Based on the foregoing, it should be appreciated that there is a need for improved apparatuses and methods that address these and/or other perceived shortcomings of the prior art. For example, there is a need for apparatuses and methods for subretinal fluid drainage that significantly minimize or eliminate the occurrence of hemorrhage while eliminating the need to perform a sclerotomy, thereby reducing the time for surgery, and also permitting the viewing of the subretinal fluid drainage under direct observation with a binocular indirect ophthalmoscope.

SUMMARY OF THE INVENTION

The present invention provides apparatuses and methods for transcleral cautery and subretinal drainage.

Briefly described, one embodiment of the apparatus, among others, includes a barrel section. A needle section extends from the barrel section. Additionally, a scleral depressor section at least partially surrounds an intermediate portion of the needle section.

Another embodiment of the apparatus includes an inner barrel section and an outer barrel section. An inner needle section extends from the inner barrel section, and an outer needle section extends from the outer barrel section. Additionally, a scleral depressor section at least partially surrounds an intermediate portion of the outer needle section. The outer needle section and the outer barrel section are adapted to receive the inner needle section and the inner barrel section therein such that the distal end of the inner needle section can be withdrawn inside of the outer needle section and at least partially extended outside of the outer needle section.

The present invention can also be viewed as providing a method for transcleral cautery and subretinal drainage. In this regard, one embodiment of such a method, among others, can be broadly summarized by the following steps: providing an apparatus for use with an eye that includes a barrel section, a needle section, a scleral depressor section, and a cautery section, inserting the needle section into the sclera and choroid of the eye, cauterizing the choroid of the eye with the cautery section, further inserting the needle section into the retinal pigment epithelium and the subretinal space of the eye, and draining at least part of the subretinal fluid contained in the eye into the needle section.

Another embodiment of the method can be broadly summarized by the following steps: providing an apparatus for use with an eye that includes an inner barrel section, an inner needle section, an outer barrel section, an outer needle section, a scleral depressor section, and a cautery section, inserting the outer needle section into the sclera and choroid of the eye, cauterizing the choroid of the eye with the cautery section, inserting the inner needle section into the retinal pigment epithelium and the subretinal space of the eye, and draining at least part of the subretinal fluid contained in the eye into the inner needle section.

Other apparatuses, methods, features, and advantages of the present invention will be or become apparent to one with skill in the art upon examination of the following drawings and detailed description. It is intended that all such additional apparatuses, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Having summarized the invention above, reference is now made in detail to the figures which depict exemplary embodiments of the invention. Generally, the invention provides apparatuses and methods for the performance of transcleral cautery and subretinal drainage. Referring to FIGS. 1A-1D, an embodiment of a single barrel/single needle transcleral cautery/subretinal drainage apparatus 100 (hereafter, the "single barrel apparatus") is shown.

The single barrel apparatus 100 includes a barrel section 102 that is connected to a needle section 104. Typically, although not exclusively, both the barrel section 102 and the needle section 104 are substantially cylindrical in shape. Further, the needle section 104 typically has a substantially smaller diameter than the diameter of the barrel section 102, as depicted, for example, in FIGS. 1A-1D. The barrel section 102 may include a transition section 106 that transitions in diameter from substantially the diameter of the barrel section 102 to substantially the diameter of the needle section 104 such that fluid or other material may be transferred from the needle section 104 to the barrel section 102 and/or the converse.

Typically, the barrel section 102, including the transition section 106, is constructed of a glass or plastic material, but other materials may be used within the scope of the invention.

The needle section 104 is typically constructed of a metal, such as stainless steel or aluminum, but the needle section 104 may also be constructed of other materials within the scope of the invention.

As depicted in the various views of the single barrel apparatus 100 shown in FIGS. 1A-1D, both the barrel section 102 and the needle section 104 define an interior volume. The interior volume of each section is adapted to contain fluid or other material. In some embodiments, the end of the barrel section 102 opposite the needle section 104 may be closed off or sealed. In other embodiments, the barrel section 102 may include an opening at the end opposite the needle section 104, and this opening may exhibit a diameter that is larger, smaller, or substantially the same as the diameter of the barrel section 102. In such embodiments, the opening of the barrel section 102 may be connected to some other component (not shown), for example a flexible tubing. Such other component may serve the purpose, for example, of conveying fluid or other material into or out of the barrel section 102.

The needle section 104 includes an opening at the distal end (i.e., the end opposite the barrel section 102). This opening is typically substantially the same diameter as the diameter of the needle section 104, but may be larger or smaller in diameter than that of the needle section 104. The opening of the needle section 104 is adapted to accept or discharge fluid or other material, particularly in the performance of eye surgery. The opening of the needle section 104 is typically also adapted to cut or pierce organic tissues, such as scleral, choroidal, and retinal tissue of an eye. For example, the opening may be shaped and further adapted such that it exhibits a sharp end surface. A typical outer diameter for the needle section 104 is 1.0 mm, although other diameters may be implemented within the scope of the invention.

The single barrel apparatus includes additional features that make it useful for the above mentioned cautery and drainage functions. In that regard, the single barrel apparatus 100 may further include a scleral depressor section 108 and/or a cautery section 110. The scleral depressor section 108 is typically substantially circular and has a larger diameter than that of the needle section 104. The scleral depressor section 108 is typically composed of a material that is substantially non-conductive of heat and/or electrical current. For example, the scleral depressor section 108 may be composed of a glass, aluminum, or plastic material that possesses the foregoing characteristics. The scleral depressor section 108 at least partially surrounds the needle section 104 and is typically securely affixed to the needle section 104. Some embodiments of the single barrel apparatus 100 may not include the scleral depressor section 108.

Figure 1A:
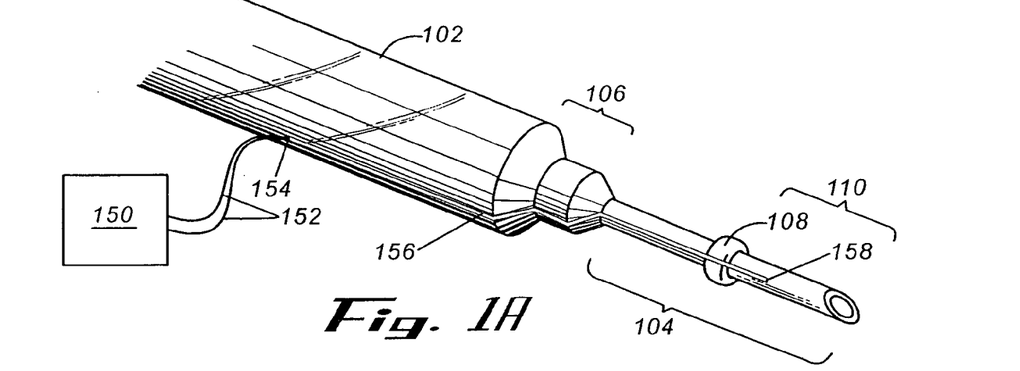
FIG. 1A is a perspective view of an embodiment of a single barrel/single needle transcleral cautery/subretinal drainage apparatus of the present invention.
Figure 1B:
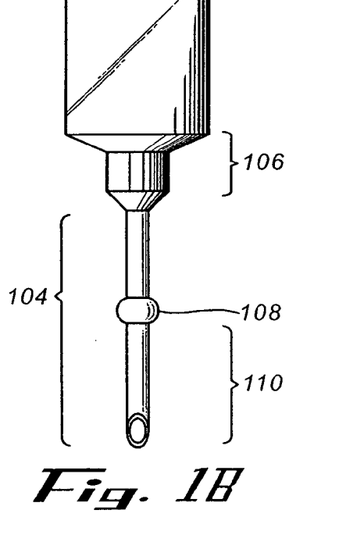
FIG. 1B is a front view of an embodiment of a single barrel/single needle transcleral cautery/subretinal drainage apparatus of the present invention.
Figure 1C:
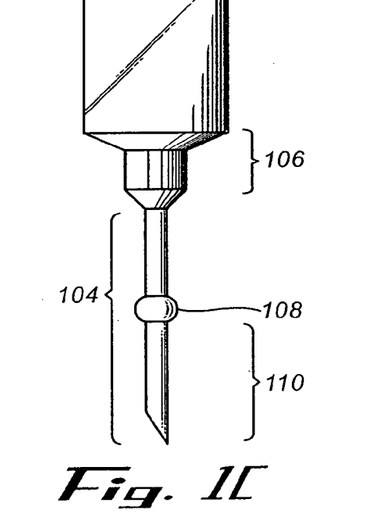
FIG. 1C is a side view of an embodiment of a single barrel/single needle transcleral cautery/subretinal drainage apparatus of the present invention.
Figure 1D:
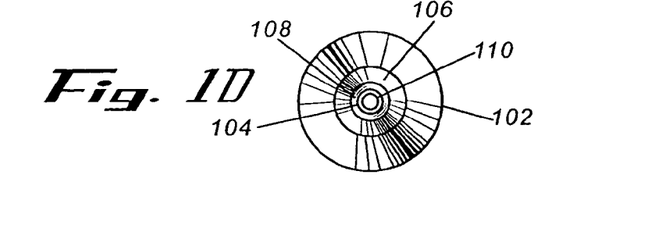
FIG. 1D is a bottom view of an embodiment of a single barrel/single needle transcleral cautery/subretinal drainage apparatus of the present invention.

The cautery section 110 is typically located at the distal portion of the needle section 104 beyond the scleral depressor section 108, as depicted, for example, in FIGS. 1A-1C. Typically, although not exclusively, the distance from the distal end (i.e., the opening) of the needle section 104 to the scleral depressor section 108 is 1.5 mm and the radial distance from the outer surface of the needle section 104 to the outer edge of the scleral depressor section 108 is 2.5 mm.

The cautery section 110 is adapted to cauterize tissue or other material that it contacts. The cautery section 110 is typically heated by energy supplied from an energy supplying device 150 as depicted in FIG. 1A, such as a cautery machine. Typically, only the cautery section 110 is heated while the other portions of the needle section 104 maintain a lower or substantially ambient temperature as a result of, for example, the temperature gradient characteristics of the needle section 104 or the other portions being substantially insulated from heating.

Heating of the cautery section 110 may be accomplished in various ways. For example, as shown in FIG. 1A, one or more energy carrying conductors 152, such as insulated wires, may carry energy from the energy supplying device 150 to an attachment point 154 on the barrel section 102. From such connection point 154 to the cautery section 110, insulation or sheathing 156 may be provided around the conductors 152 to consolidate the conductors 152 and prevent heating of sections other than the cautery section 110. The conductors 152 are connected to the cautery section 110 at a termination point 158. The termination point 158 may be accomplished in various ways so that energy supplied from the energy supplying device 150 causes the heating of the cautery section 110. For example, a portion of the conductors 152 may be soldered to or wrapped around a portion of the cautery section 110. Other variations and devices may be implemented to heat the cautery section 110 and are considered to be within the scope of the present invention.

Referring now to FIGS. 2A-2D, an embodiment of a two barrel/two needle transcleral cautery/subretinal drainage apparatus 200 (hereafter, the "two barrel apparatus") is shown. The two barrel apparatus 200 includes several components. There is an outer barrel section 202 that is connected to an outer needle section 204. The outer barrel section 202 and the outer needle section 204 are typically, although not exclusively, substantially cylindrical in shape. Further, as depicted in FIGS. 2A-2D, the diameter of the outer barrel section 202 is typically larger than the diameter of the outer needle section 204. Accordingly, the outer barrel section 202 may include an outer transition section 206 that transitions in diameter from substantially the diameter of the outer barrel section 202 to substantially the diameter of the outer needle section 204 such that fluid or other material may be transferred from the outer needle section 204 to the outer barrel section 202 and/or the converse.

The outer barrel section 202, including the outer transition section 206, is typically constructed of a glass or plastic material, but other materials may be applied within the scope of the invention. The outer needle section 204 is typically constructed of a metal, such as stainless steel or aluminum, but the outer needle section 204 may alternatively be constructed of other materials within the scope of the invention.

Both the outer barrel section 202 and the outer needle section 204 define an interior volume as depicted, for example, in the various views of the two barrel apparatus 200 shown in FIGS. 2A-2D. In some embodiments, the outer barrel section 202 may be closed off or sealed at the end opposite the outer needle section 204 In other embodiments, the outer barrel section 202 may include an opening at the end opposite the outer needle section 204, and this opening may exhibit a diameter that is larger, smaller, or substantially the same as the diameter of the outer barrel section 202.

The outer needle section 204 includes an opening at the distal end (i.e., the end opposite the outer barrel section 202) as depicted, for example, in the various views of the two barrel apparatus 200 shown in FIGS. 2A-2D. This opening is typically substantially the same diameter as the diameter of the outer needle section 204, but may be larger or smaller in diameter than that of the outer needle section 204. The opening of the outer needle section 204 is typically also adapted to cut or pierce organic tissues, such as scleral, choroidal, and retinal tissue of an eye. For example, the opening may be shaped and further adapted such that it exhibits a sharp end surface. A typical outer diameter for the outer needle section 204 is 1.0 mm, although other diameters may be implemented within the scope of the invention.

The two barrel apparatus 200 may also include a scleral depressor section 208 and a cautery section 210. The scleral depressor section 208 is typically substantially circular and has a larger diameter than that of the outer needle section 204. The scleral depressor section 208 is typically composed of a material that is substantially non-conductive of heat and/or electrical current. For example, the scleral depressor section 208 may be composed of a glass, aluminum, or plastic material that possesses the foregoing characteristics. The scleral depressor section 208 at least partially surrounds the outer needle section 204 and is typically securely affixed to the outer needle section 204. Some embodiments of the two barrel apparatus 200 may not include the scleral depressor section 208.

The cautery section 210, as depicted for example in FIGS. 2A-2D, is typically located at the distal portion of the outer needle section 204 beyond the scleral depressor section 208. Typically, although not exclusively, the distance from the distal end (i.e., the opening) of the outer needle section 204 to the scleral depressor section 208 is 1.5 mm and the radial distance from the outer surface of the outer needle section 204 to the outer edge of the scleral depressor section 208 is 2.5 mm.

Figures 2A, 2B, 2C:
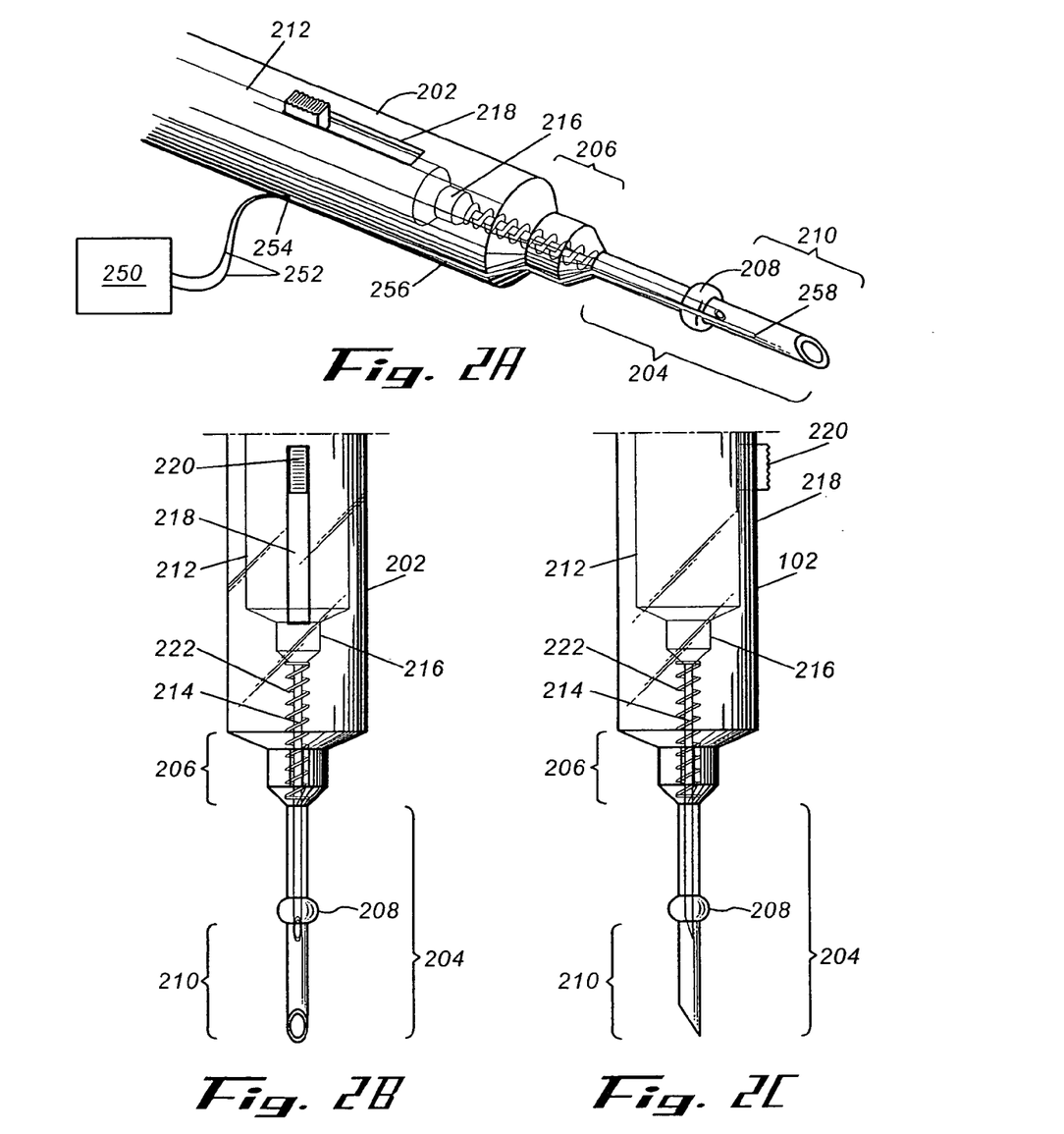
FIG. 2A is a perspective view of an embodiment of a two barrel/two needle transcleral cautery/subretinal drainage apparatus of the present invention.
FIG. 2B is a front view of an embodiment of a two barrel/two needle transcleral cautery/subretinal drainage apparatus of the present invention.
FIG. 2C is a side view of an embodiment of a two barrel/two needle transcleral cautery/subretinal drainage apparatus of the present invention.
Figure 2D:
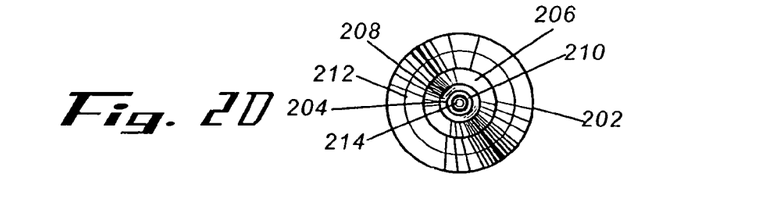
FIG. 2D is a bottom view of an embodiment of a two barrel/two needle transcleral cautery/subretinal drainage apparatus of the present invention.

The cautery section 210 is adapted to cauterize tissue or other material that it contacts. The cautery section 210 is typically heated by energy supplied from an energy supplying device 250 as depicted in FIG. 2A, such as a cautery machine. Typically, only the cautery section 210 is heated while the other portions of the outer needle section 204 maintain a lower or substantially ambient temperature as a result of, for example, the temperature gradient characteristics of the outer needle section 204 or the other portions being substantially insulated from heating.

Heating of the cautery section 210 may be accomplished in various ways. For example, as shown in FIG. 2A, one or more energy carrying conductors 252, such as insulated wires, may carry energy from the energy supplying device 250 to an attachment point 254 on the outer barrel section 202. From such connection point 254 to the cautery section 210, insulation or sheathing 256 may be provided around the conductors 252 to consolidate the conductors 252 and prevent heating of sections other than the cautery section 210. The conductors 252 are connected to the cautery section 210 at a termination point 258. The termination point 258 may be accomplished in various ways so that energy supplied from the energy supplying device 250 causes the heating of the cautery section 210. For example, a portion of the conductors 252 may be soldered to or wrapped around a portion of the cautery section 210. Other variations and devices may be implemented to heat the cautery section 210 and are considered to be within the scope of the present invention.

As discussed above, the outer barrel section 202 and the outer needle section 204 each define an interior volume. The interior volume of each section is adapted to receive and contain an inner barrel section 212 that is connected to an inner needle section 214. Typically, although not exclusively, the inner barrel section 212 and the inner needle section 214 are substantially cylindrical in shape. As depicted in FIGS. 2A-2D, the inner barrel section 212 typically has a larger diameter than the inner needle section 214. Further, the inner barrel section 212 may include an inner transition section 216 that transitions in diameter from substantially the diameter of the inner barrel section 212 to substantially the diameter of the inner needle section 214 such that fluid or other material may be transferred from the inner needle section 214 to the inner barrel section 212 and/or the converse.

The inner barrel section 212, including the inner transition section 216, is typically constructed of a glass or plastic material, but other materials may be applied within the scope of the invention. The inner needle section 214 is typically constructed of a metal, such as stainless steel or aluminum, but the inner needle section 214 may alternatively be constructed of other materials within the scope of the invention.

The diameters and overall dimensions of the inner barrel section 212 and the inner needle section 214 are such that these sections can be at least partially received within the outer barrel section 202 and the outer needle section 204 as depicted, for example, in FIGS. 2A-2D. Thus, in a typical configuration of the two barrel apparatus 204, the inner barrel section 202 is received within the outer barrel section 212 and the inner needle section 214 is received within the outer needle section 204. Further, the outer barrel section 202 and the outer needle section 204 are adapted to facilitate movement of the inner barrel section 212 and the inner needle section 214 such that the inner needle section 214 can be varied in position from being partially extended outside of the outer needle section 204 to being partially withdrawn within the outer barrel section 202. The positioning of the inner needle section 214 when it is partially withdrawn within the outer barrel section 202 is such that the heating of the cautery section 210 does not cause any substantial heating of the inner needle section 214 and the inner needle section 214 does not extend out of the opening of the outer needle section 204.

To further facilitate the movement of the inner barrel section 212 and inner needle section 214 within the outer barrel section 202 and the outer needle section 204, the outer barrel 204 may have a side opening 218, such as a slot. The inner barrel section 212 may be configured such that a portion of it protrudes out of the side opening 218 when the inner barrel section 212 is received within the outer barrel section 202, and this protruding portion 220 can be manipulated to move the combined structure of the inner barrel section 212 and inner needle section 214 within the combined structure of the outer barrel section 202 and the outer needle section 204. In some embodiments, the protruding portion 220 of the inner barrel section 212 may be a knob or other element attached to the side of the inner barrel section 212.

Another feature that the two barrel apparatus 200 may include to facilitate the movement of the combined structure of the inner barrel section 212 and inner needle section 214 within the combined structure of the outer barrel section 202 and outer needle section 204 is an elastic compressible element 222, such as a normally decompressed helical spring. As depicted for example in FIGS. 2A-2C, the elastic compressible element 222 is typically positioned such that one end of the elastic compressible element 222 rests against an interior portion of the outer barrel section 212, for example, at the outer transaction section 206. The other end of the elastic compressible element 222 typically rests against an exterior portion of the inner barrel section 212, for example, at the inner transition section 216. Further, as depicted in FIGS. 2A-2C, the elastic compressible element 222 may partially surround or encircle the inner needle section 214. As described in this embodiment, the elastic compressible element 222 serves to retract and maintain the combined structure of the inner barrel section 212 and inner needle section 214 in a fully withdrawn position within the combined structure of the outer barrel section 202 and outer needle section 204.

Focusing in further detail on the inner barrel section 212 and the inner needle section 214 of the two barrel apparatus 200, in some embodiments, the end of the inner barrel section 212 opposite the inner needle section 214 may be closed off or sealed. In other embodiments, the inner barrel section 212 may include an opening at the end opposite the inner needle section 214. This opening may exhibit a diameter that is larger, smaller, or substantially the same as the diameter of the inner barrel section 212. In such embodiments, the opening of the inner barrel section 212 may be connected to some other component (not shown), for example a flexible tubing, that may serve the purpose, for example, of conveying fluid or other material into or out of the inner barrel section 212.

The inner needle section 214, as depicted in the various views of the two barrel apparatus 200 shown in FIGS. 2A-2D, includes an opening at the end opposite the inner barrel section 212. This opening is typically substantially the same diameter as the diameter of the inner needle section 214, but may be larger or smaller in diameter than that of the inner needle section 214 as well. The opening of the inner needle section 214 is adapted to accept or discharge fluid or other material, particularly in the performance of eye surgery. The opening of the inner needle section 214 is typically also adapted to cut or pierce organic tissues, such as scleral, choroidal, and retinal tissue of an eye. For example, the opening may be shaped and further adapted such that it exhibits a sharp end surface.

Having discussed several apparatus embodiments of the present invention, discussion is now focused on several related method embodiments. Although descriptions of various embodiments are presented hereafter with respect to surgery on a human eye, the application of the embodiments to other types of eyes is not excluded from being within the scope of the invention. In this regard, a method for performing transcleral cautery and subretinal drainage using, for example, the single barrel apparatus 100 in accordance with an embodiment of the present invention is described hereafter.

Figure 3A:
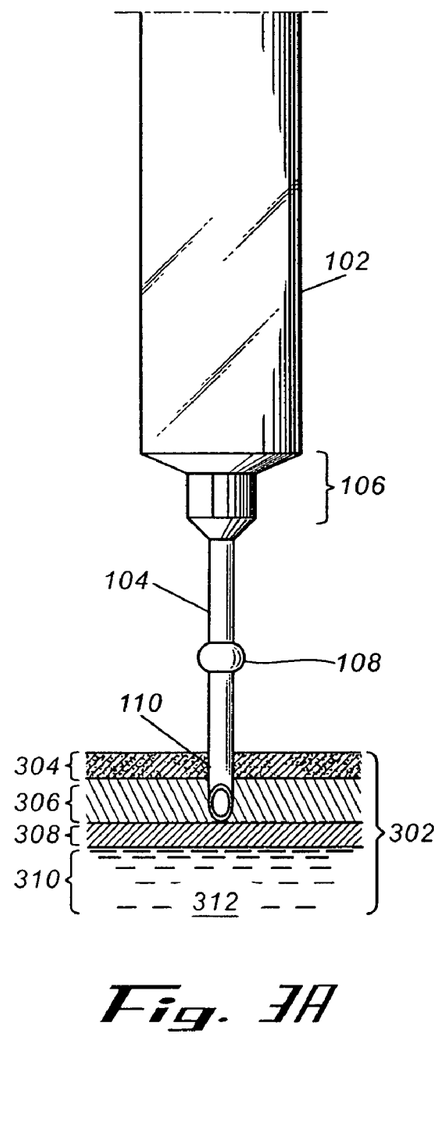
FIG. 3A shows an embodiment of a single barrel/single needle transcleral cautery/subretinal drainage apparatus of the present invention partially inserted into an eye section.
Figure 3B:
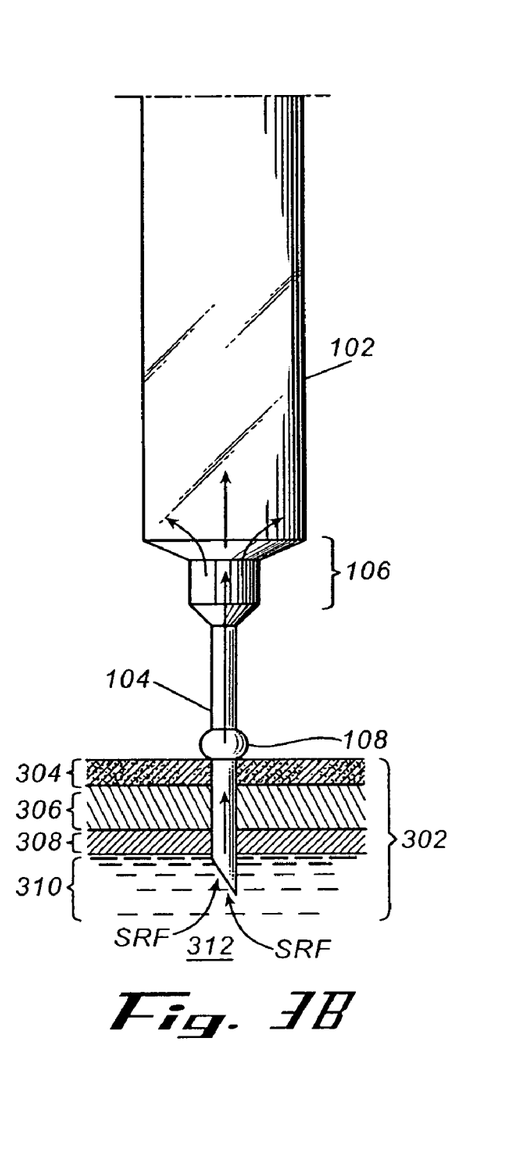
FIG. 3B shows an embodiment of a single barrel/single needle transcleral cautery/subretinal drainage apparatus of the present invention fully inserted into an eye section.

FIGS. 3A-3B depict the single barrel apparatus 100 inserted into an eye section 302 of a human eye to perform transcleral cautery and subretinal drainage. The features of the single barrel apparatus 100 were described above with respect to FIGS. 1A-1D. In FIGS. 3A-3B, the eye section 302 of the eye includes several sections that are relevant to this description. The sclera 304 is the outermost section of the eye with respect to this discussion. As is known, a typical thickness of the sclera 304 is approximately 0.45 mm to 1.3 mm with a thickness of approximately 1.1 mm at the equator. Below (i.e., inside of) the sclera 304 is the choroid 306. The choroid 306 has a typical thickness of approximately 0.2 mm. Below (i.e., inside of) the choroid 306 is the retinal pigment epithelium ("RPE") 308, and below (i.e., inside of) the RPE 308 is the subretinal space 310 which will contain subretinal fluid ("SRF") 312 when, for example, there is a retinal detachment condition of the eye.

FIG. 3A depicts the typical positioning of the single barrel apparatus 100 to perform transcleral cautery (which includes cautery of the choroid 306). In that regard, the needle section 104 is inserted into the eye section 302 such that it penetrates the sclera 304 and the choroid 306 with the cautery section 110 of the needle section 104 being positioned in contact with the choroid 306. During such insertion of the needle section 104, the scleral depressor section 108 may contact the sclera 304. With the needle section 104 placed in the foregoing position with respect to the eye section 302, transcleral cautery may be performed by heating the cautery section 110 of the needle section 104 appropriately. Such heating may be controlled for example, by varying the energy supplied to the cautery section 110 from an energy supplying device such as a cautery machine (not shown).

FIG. 3B depicts the typical positioning of the single barrel apparatus 100 to perform drainage of subretinal fluid 312. In that regard, the needle section 104 is inserted into the eye section 302 such that it penetrates through the sclera 304, the choroid 306, the RPE 308, and into the subretinal space 310 so that the opening of the needle section 104 is exposed to the subretinal fluid 312 and the subretinal fluid 312 may pass into the needle section 104 and subsequently into the barrel section 102 of the single barrel apparatus 100. During such insertion of the needle section 104, the scleral depressor section 108 may contact the sclera 304. The scleral depressor section 108 may also serve to limit the insertion depth of the needle section 104 into the eye section 302.

To facilitate the accurate insertion and positioning of the single barrel apparatus 100 into the eye section 302, direct visualization into the eye may be performed using a binocular indirect ophthalmoscope. Typically, the scleral depressor section 108 is used prior to the initial insertion of the needle section 104 into the eye section 302 to depress the sclera 304 such that a surgeon using a binocular indirect ophthalmoscope can determine an optimal insertion point of the needle section 104 into the eye section 302. The drainage of subretinal fluid 312 into the needle section 104 and subsequently into the barrel section 102 typically is accomplished as a result of positive pressure of the eye and capillary action. Pressure applied to the eye as a result of the contact of the sclera 304 by, for example, the scleral depressor section 108, a scleral buckle, and/or a cotton tipped applicator may further facilitate the drainage of subretinal fluid 312 into the needle section 104.

While performing a surgical procedure using the single barrel apparatus 100, the steps of penetrating the eye section 302, cauterizing the choroid 306, and draining subretinal fluid 312 may each be performed repeatedly as needed in order to facilitate the surgery.

Figure 4A:
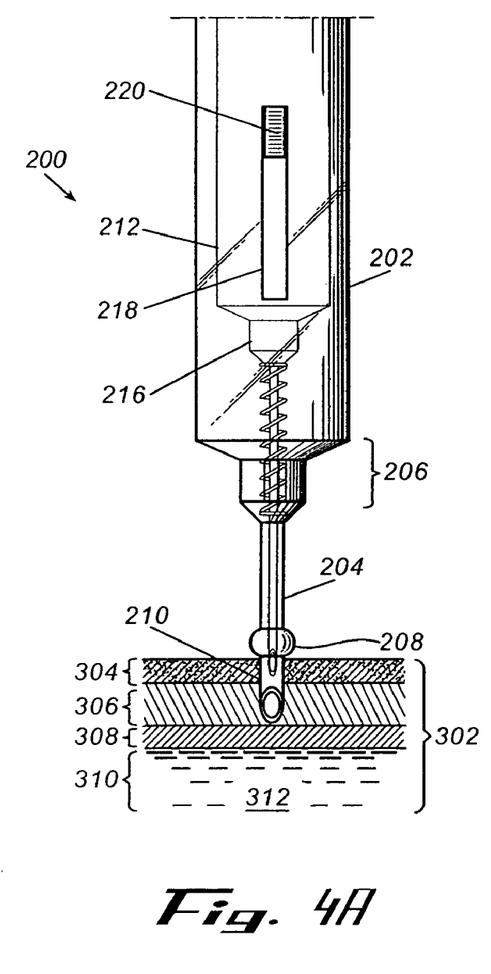
FIG. 4A shows an embodiment of a two barrel/two needle transcleral cautery/subretinal drainage apparatus of the present invention partially inserted into an eye section.
Figure 4B:
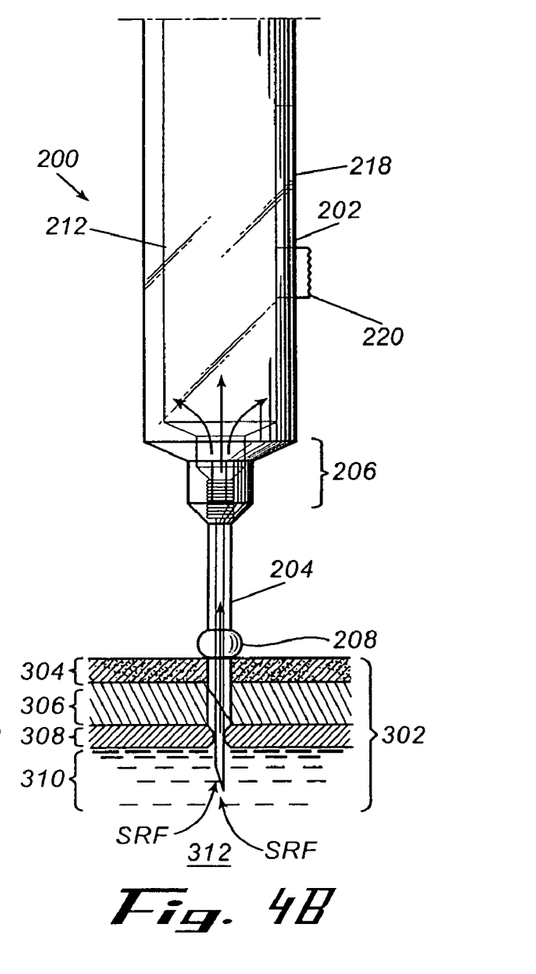
FIG. 4B shows an embodiment of a two barrel/two needle transcleral cautery/subretinal drainage apparatus of the present invention fully inserted into an eye section.

In accordance with another embodiment of the present invention, a method is now described for performing transcleral cautery and subretinal drainage using, for example, the two barrel apparatus 200. In that regard, FIGS. 4A-4B depict the two barrel apparatus 200 inserted into an eye section 302 of a human eye to perform transcleral cautery and subretinal drainage. The features of the two barrel apparatus 200 were described in detail above with respect to FIGS. 2A-2D. In FIGS. 4A-4B, the eye section 302 has the same features as described above with respect to FIG. 3. Thus, the eye section 302 in FIGS. 4A-4B has a sclera 304, choroid 306, RPE 308, subretinal space 310, and subretinal fluid 312, as depicted.

FIG. 4A depicts the typical positioning of the two barrel apparatus 200 to perform transcleral cautery (which includes cautery of the choroid 306). In that regard, the outer needle section 204 is inserted into the eye section 302 such that it penetrates the sclera 304 and the choroid 306 with the cautery section 210 of the needle section 204 being positioned in contact with the choroid 306. During such insertion of the outer needle section 204, the scleral depressor section 208 may contact the sclera 304. The scleral depressor section 208 may also serve to limit the insertion depth of the outer needle section 204 into the eye section 302.

With the outer needle section 204 placed in the foregoing position with respect to the eye section 302, transcleral cautery may be performed by heating the cautery section 210 of the outer needle section 204 appropriately. Such heating may be controlled for example, by varying the energy supplied to the cautery section 210 from an energy supplying device such as a cautery machine.

During the performance of transcleral cautery as described in the foregoing, the combined structure of the inner barrel section 212 and inner needle section 214 may be received within the combined structure of the outer barrel section 202 and outer needle section 204 such that the inner needle section 214 is at least partially withdrawn into the outer needle section 204, as shown for example in FIG. 4A. In such position, the heating of the cautery section 210 does not cause any substantial heating of the inner needle section 214 and the inner needle section 214 does not extend out of the opening of the outer needle section 204. Alternatively, in some embodiments, the combined structure of the inner barrel section 212 and inner needle section 214 may be completely withdrawn outside of the combined structure of the outer barrel section 202 and the outer needle section 204 during the performance of transcleral cautery.

FIG. 4B depicts the typical positioning of the two barrel apparatus 200 to perform drainage of subretinal fluid 312. In that regard, the combined structure of the outer barrel section 202 and outer needle section 204 are positioned the same as for the performance of transcleral cautery. Thus, drainage of subretinal fluid 312 can be performed with the two barrel apparatus 200 in the same position that transcleral cautery (including cautery of the choroid 306) can be performed with the two barrel apparatus 200. Therefore, as depicted in FIG. 4B, the outer needle section 204 is inserted into the eye section 302 such that it penetrates the sclera 304 and the choroid 306 with the cautery section 210 of the outer needle section 204 being positioned in contact with the choroid 306. Further, during such insertion of the outer needle section 204, the scleral depressor section 208 may contact the sclera 304.

With the outer needle section 204 placed in the foregoing position with respect to the eye section 302, the combined structure of the inner barrel section 212 and inner needle section 214 are received within the combined structure of the outer barrel section 202 and outer needle section 204, as depicted in FIG. 4B, in order to perform drainage of the subretinal fluid 312. In that regard, the combined structure of the inner barrel section 212 and inner needle section 214 are positioned such that the inner needle section 214 extends partially out of the opening of the outer needle section 204 and penetrates through the RPE 308 and into the subretinal space 310, as depicted in FIG. 4B. In such position, the opening of the inner needle section 214 is exposed to the subretinal fluid 312 and the subretinal fluid 312 may pass into the inner needle section 214 and subsequently into the inner barrel section 212 of the two barrel apparatus 200.

To facilitate the accurate insertion and positioning of the two barrel apparatus 200 into the eye section 302, direct visualization into the eye may be performed using a binocular indirect ophthalmoscope. Typically, the scleral depressor section 208 is used prior to the initial insertion of the outer needle section 204 into the eye section 302 to depress the sclera 304 such that a surgeon using a binocular indirect ophthalmoscope can determine an optimal insertion point of the outer needle section 204 into the eye section 302. The drainage of subretinal fluid 312 into the inner needle section 204 and subsequently into the inner barrel section 202 typically is accomplished as a result of positive pressure of the eye and capillary action. Pressure applied to the eye as a result of the contact of the sclera 304 by, for example, the scleral depressor section 208, a scleral buckle, and/or a cotton tipped applicator may further facilitate the drainage of subretinal fluid 312 into the inner needle section 214.

While performing a surgical procedure using the two barrel apparatus 200, the outer needle section 204 can be positioned in the eye section 302 as described above and maintained in that position to perform transcleral cautery as needed. While the outer needle section 204 is inserted appropriately into the eye section 302, the inner needle section 214 can be inserted into and retracted out of the subretinal space 310 in order to perform drainage of subretinal fluid 312 as needed. In that regard, the protruding portion 220 of the inner barrel section 212 (described above with respect to FIGS. 2A-2D) may facilitate the insertion and retraction of the inner needle section 214 from the subretinal space 310 and the RPE 308. For example, a surgeon may position his finger, thumb, etc. on the protruding portion 220 in a manner to cause the inner needle section 214 to be inserted or retracted from the subretinal space 310 and the RPE 308.

Additionally, or alternatively, the elastic compressible element 222 (described above with respect to FIGS. 2A-2D) may also facilitate the insertion and/or retraction of the inner needle section 214 from the subretinal space 310 and the RPE 308. For example, with the elastic compressible element 222 positioned, for example, as shown in FIGS. 4A-4B, the inner needle section 214 will be retracted from the subretinal space 310 and the RPE 308 when no force is applied, for example to the protruding portion 220 of the inner barrel section 202, to cause the inner needle section 214 to insert into the RPE 308 and the subretinal space 310.

The single barrel apparatus 100 and the two barrel apparatus 200, described in the foregoing, may be implemented to facilitate the performance of various types of eye surgery. For example, the single barrel apparatus 100 and the two barrel apparatus 200 may each be used to perform transcleral cautery and subretinal fluid drainage to facilitate traditional scleral buckle surgery or pneumatic retinopexy.

It should be emphasized that the above-described embodiments of the present invention are merely possible examples of implementations merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

The invention claimed is:

1. An apparatus for use with an eye having a sclera, a choroid, and subretinal fluid, said apparatus comprising:
   a barrel section having a first wall configured to define a first interior volume and adapted to retain fluid therein;
   a needle section, extending from said barrel section, having a second wall defining a second interior volume and adapted to retain fluid therein, said needle section being in fluidic communication with said barrel section and being operative to retain the subretinal fluid of an eye that flows between said needle section and said barrel section when the subretinal fluid of the eye is drained into said needle section; and
   a scleral depressor section at least partially surrounding an intermediate portion of said needle section and adapted to engage and depress the sclera of the eye, said scleral depressor section being annular in shape and having a smooth exterior surface positioned to contact the sclera of the eye as said needle section engages the choroid of the eye, further comprising a cautery section of said needle section between said scleral depressor section and the distal end of said needle section, said cautery section being adapted to cauterize the choroid of the eye; and further comprising an energy supplying device configured to supply energy to said cautery section such that said cautery section is heated for cauterizing the choroid of the eye.

2. The apparatus of claim 1, wherein said barrel section and said needle section are cylindrically shaped.

3. The apparatus of claim 1, wherein:
   said barrel section has an inner barrel section and an outer barrel section;
   said needle section has an inner needle section and an outer needle section;
   said inner barrel section has a first inner wall configured to define a first interior volume and adapted to retain fluid therein;
   said inner needle section, extending from said inner barrel section, has a second inner wall defining a second interior volume and adapted to retain fluid therein, said inner needle section being in fluidic communication with said inner barrel section such that the subretinal fluid of the eye is retained within and flows between said inner needle section and said inner barrel section when the subretinal fluid of the eye is drained into said inner needle section;
   said outer barrel section has a first outer wall configured to define a third interior volume;
   said outer needle section, extending from said outer barrel section, has a second outer wall defining a fourth interior volume, said outer needle section and said outer barrel section being adapted to receive said inner needle section and said inner barrel section therein such that the distal end of said inner needle section can be withdrawn inside of said outer needle section and at least partially extended outside of said outer needle section; and
   a said scleral depressor section at least partially surrounds said outer needle section.

4. The apparatus of claim 3, further comprising a protruding section protruding at least partially along the length of said inner barrel section, and wherein said outer wall has a longitudinal opening extending at least partially along the length of said outer barrel section such that said protruding section protrudes through said longitudinal opening when said inner barrel section is received within said outer barrel section, said longitudinal opening being adapted such that said protruding section is slideably engageable to cause said inner needle section to move fully inside of said outer needle section and at least partially outside of said outer needle section.

5. The apparatus of claim 4, further comprising an elastic compressible element positioned within said outer barrel section and engaging between the interior of said outer barrel section and the exterior of said inner barrel section such that said elastic compressible element causes said inner needle section to be at least partially withdrawn inside of said outer needle section when said protruding section is not slideably engaged.

6. The apparatus of claim 5, wherein said elastic compressible element is a normally decompressed helical spring.

7. The apparatus of claim 3, wherein said inner barrel section, said outer barrel section, said inner needle section, and said outer needle section are cylindrically shaped.

8. The apparatus of claim 1, wherein said exterior surface curves rearward, toward said barrel section, from an inner diameter of a distal end of said scleral depressor section.

9. The apparatus of claim 1, wherein a distance between a distal end of said scleral depressor section and a distal end of said needle section is approximately 1.5 mm.

10. The apparatus of claim 1, wherein said scleral depressor section extends radially outwardly from said needle section by a distance of approximately 2.5 mm.

* * * * *